United States Patent
Folestad et al.

(10) Patent No.: US 6,946,157 B2
(45) Date of Patent: *Sep. 20, 2005

(54) METHOD AND APPARATUS FOR MONITORING THE COATING ON PARTICLE DURING MANUFACTURING OF A PHARMACEUTICAL PRODUCT

(75) Inventors: Staffan Folestad, Västra Frölunda (SE); Ingela Niklasson Björn, Gothenburg (SE); Anders Rasmuson, Mölndal (SE); Daniel Ström, Gothenburg (SE)

(73) Assignee: AstraZeneca AB, Sodertalje (SE)

( * ) Notice: Subject to any disclaimer, the term of this patent is extended or adjusted under 35 U.S.C. 154(b) by 246 days.

This patent is subject to a terminal disclaimer.

(21) Appl. No.: 09/806,795

(22) PCT Filed: Jan. 8, 2001

(86) PCT No.: PCT/SE01/00023

§ 371 (c)(1),
(2), (4) Date: Apr. 4, 2001

(87) PCT Pub. No.: WO01/51915

PCT Pub. Date: Jul. 19, 2001

(65) Prior Publication Data

US 2002/0136822 A1 Sep. 26, 2002

(30) Foreign Application Priority Data

Jan. 13, 2000 (SE) ............................................. 0000090

(51) Int. Cl.⁷ ............................ B01J 13/00; B05C 11/00
(52) U.S. Cl. .................... 427/2.15; 427/2.14; 427/9; 427/213; 427/372.2; 427/421.1; 427/424; 118/663; 118/665; 118/690; 118/691; 118/712; 356/336; 356/337

(58) Field of Search .................... 427/2.1, 2.14, 427/2.15, 2.16, 8, 9, 10, 212, 213, 214, 215, 220, 372.2, 384.4, 421, 424, 427, 421.1; 118/663, 665, 668, 690, 691, 712; 356/336, 337

(56) References Cited

U.S. PATENT DOCUMENTS 4,125,391 A * 11/1978 Van Laethem ............. 65/60.51
4,993,264 A * 2/1991 Cody et al. ................... 73/579

(Continued)

FOREIGN PATENT DOCUMENTS

WO          0003229          1/2000

OTHER PUBLICATIONS

Watano, S. et al., "Control of Granulation Process by Fuzzy Logic", in North American Fuzzy Information, 1999, 905–908.

(Continued)

*Primary Examiner*—Elena Tsoy
(74) *Attorney, Agent, or Firm*—White & Case LLP

(57) ABSTRACT

In a method of monitoring the formation of a coating on a single particle (P), an apparatus is used which comprises means (2,5,6,9) for arranging said particle (P) at a given spatial location, and a fluid supply unit (3) adapted to apply a coating fluid to the particle (P) such that the coating is formed. Further, the apparatus has a measurement unit (4) which is adapted to perform a spectrometric measurement on the coating during formation thereof, and to derive a measurement value of at least one principle parameter related to the coating. This, such principle parameters, for example the thickness, thickness growth rate and physical and/or chemical properties related to the quality of the coating, as well as heat, mass and momentum transfer, can be continuously and non-invasively monitored during the coating process on the single particle (P). The results of such measurements can be used to understand the coating process on the single particle (P), and ultimately to control, up-scale and develop industrial full-scale coating plants.

50 Claims, 1 Drawing Sheet

U.S. PATENT DOCUMENTS

| | | | | |
|---|---|---|---|---|
| 5,091,278 A | * | 2/1992 | Teuscher et al. | 430/58.05 |
| 5,420,681 A | * | 5/1995 | Woodruff | 356/326 |
| 5,518,759 A | * | 5/1996 | Sevillano et al. | 423/446 |
| 5,748,311 A | * | 5/1998 | Hamann et al. | 356/336 |
| 5,750,996 A | * | 5/1998 | Drennen et al. | 250/341.2 |
| 5,784,160 A | * | 7/1998 | Naqwi | 356/496 |
| 5,871,805 A | * | 2/1999 | Lemelson | 427/10 |
| 6,038,525 A | * | 3/2000 | Maguire et al. | 702/172 |
| 6,248,363 B1 | * | 6/2001 | Patel et al. | 424/497 |

OTHER PUBLICATIONS

Laurell, T. et al., "Design and Development of a Silicon Microfabricated Flow–through Dispenser for On–Line Picolitre Sample Handling", J. Micromech. Microeng., 9 (1999), 369–376.

Link, K. et al., "Fluidized Bed Spray Granulation Investigation of the Coating Process on a Single Sphere", Chemical Engineering and Processing, 36 (1997) 443–457.

* cited by examiner

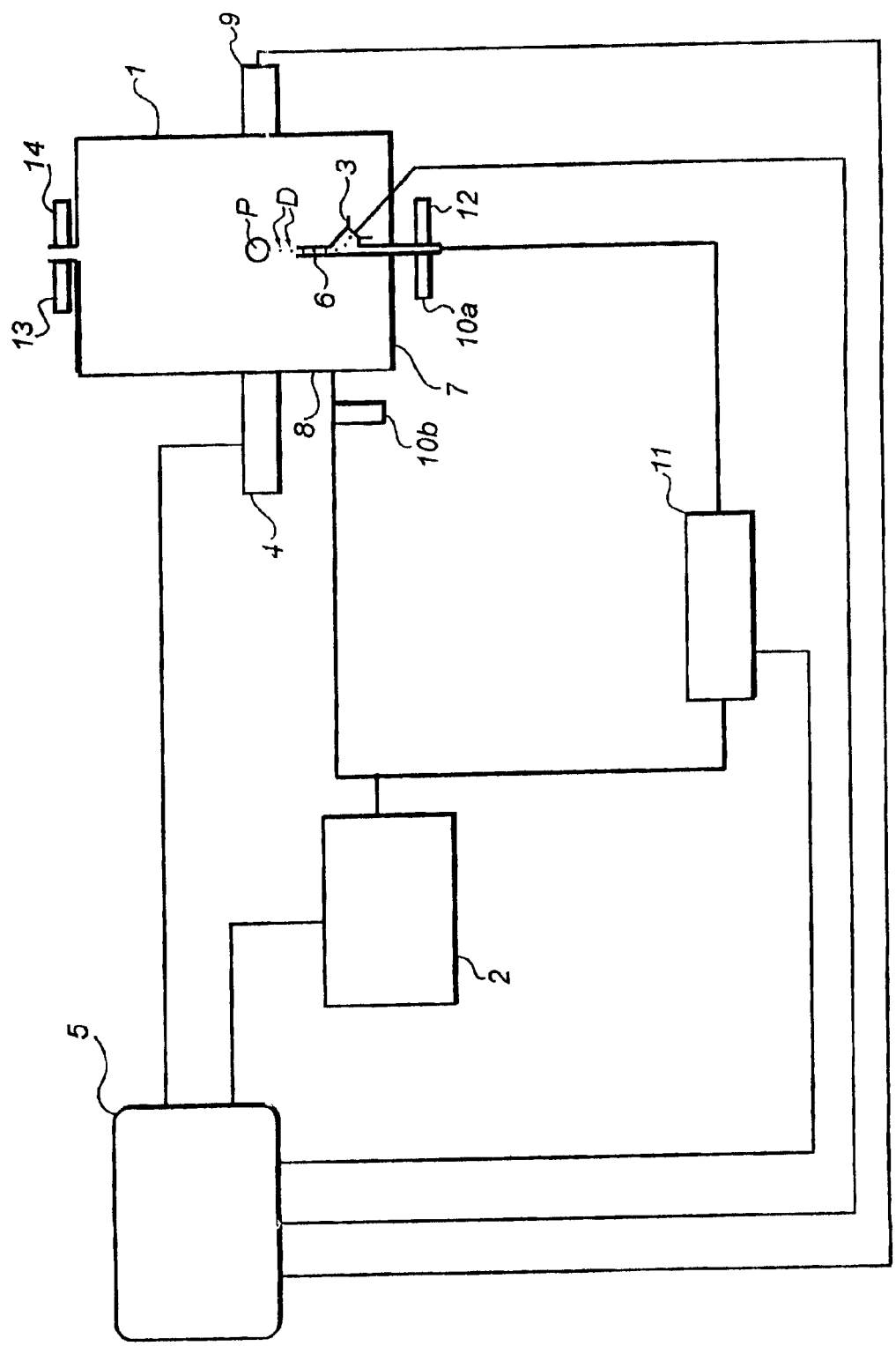

METHOD AND APPARATUS FOR MONITORING THE COATING ON PARTICLE DURING MANUFACTURING OF A PHARMACEUTICAL PRODUCT

TECHNICAL FIELD

The present invention relates to a method and apparatus for monitoring the formation of a coating on a particle. Ultimately, the invention is focused on controlling the process of manufacturing a coating of a pharmaceutical product, such as a pellet, a tablet or a capsule.

TECHNICAL BACKGROUND

Generally, a coating of a pharmaceutical product consists of one or more films and each film consists of one or more layers. Below, "coating" is used as a comprehensive expression encompassing everything from an individual layer to a combination of several different films. Each film is the result of a single coating step, generally performed in a coating vessel, where for instance layers of the film are built up. The coating process takes place either in a fluidized bed wherein particles, so-called nuclei, arc sprayed with a specific coating liquid, or by passing the particles through a spray dust of said liquid. Several other generally used coating techniques are known in the prior art, such as melting, aggregation etc. The total process of manufacturing a complete coating may involve a plurality of such coating steps. However, the process may as well be sequential, whereby the whole process represents a continuous flow.

Pharmaceutical products are coated for several reasons. A protective coating normally protects the active ingredients from possible negative influences from the environment, such as for example light and moisture but also temperature and vibrations. By applying such a coating, the active substance is protected during storage and transport. A coating could also be applied to make the product easier to swallow, to provide it with a pleasant taste or for identification of the product. Further, coatings are applied which perform a pharmaceutical function such as conferring enteric and or controlled release. The purpose of a functional coating is to provide a pharmaceutical preparation or formulation with desired properties to enable the transport of the active pharmaceutical substance through the digestive system to the region where it is to be released and/or absorbed. A desired concentration profile over time of the active substance in the body may be obtained by such a controlled course of release. An enteric coating is used to protect the product from disintegration in the acid environment of the stomach. Moreover, it is important that the desired functionalities are constant over time, i.e. during storage. By controlling the quality of the coating, the desired functionalities of the final product may also be controlled.

There are strict requirements from the different Registration Authorities on pharmaceutical products. These requirements will put high demands on the quality of the coating and require that the complex properties of the coating will be kept within narrow limits. In order to meet these demands, there is a need for accurate control of the coating process.

The quality of the coating depends on physical and/or chemical properties of the coating, such as chemical composition, local inhomogeneities, physical and chemical homogeneity, density, mechanical properties, static parameters, modulus, tensile strength, elongation at break, compression, ductility, viscoelastic parameters, morphology, macro-and microscopic properties, amorphous and/or crystallinity, permeability, porosity, aggregation, wettability, degree of coalescence/maturity, stability and ability to resist chemical and/or physical degradation. There are also other properties not listed above. The quality of the coating affects to a great extent the release properties and has a significant impact on the storage stability. In order to keep the quality of the coating within the desired narrow limits it is necessary to control the manufacturing process of the coating accurately.

In an industrial plant for coating pharmaceutical products, selected process parameters are monitored and controlled to achieve a desired quality of the end product. Such process parameters are generally global and could include, for example, the pressure in the coating vessel, the flow rate and temperature of gas and coating liquid supplied to the coating vessel, etc. However, the influence of such global process parameters of the coating process, and ultimately on the coating properties of the end product, is known only from experience in a specific plant. Thus, a processing scheme is developed for each specific plant by extensive testing. When, for example, the size or shape of the coating vessel is changed during scaling up of the process, the local environment of the particles may be altered. This calls for time-consuming measurements and adjustments in order to regain the same coating properties of the end product.

There is also a need to improve existing manufacturing processes as well as to improve existing plants. Today, this is a laborious task since the influence of any change in the process scheme or the plant design on the end product has to be investigated by extensive testing, often in full scale. The same applies to the development of new products, for example when a new type of particle or coating liquid should be used.

An attempt to fulfil the above-identified needs is disclosed in the article "Fluidized bed spray granulation, investigation of the coating process on a single sphere" by K. C. Link and E.-U. Schlünder, published in Chemical Engineering and Processing, No. 36, 1997. A laboratory-scale apparatus is designed for analysis of a single particle, in order to investigate the fundamental physical mechanisms that lead to particle growth by layering. In this apparatus, a single aluminum sphere is made to levitate on a fluidizing air flow which is supplied by a capillary tube. Thereby, the sphere is freely and rotatably suspended at a stable location in a coating vessel. An ultrasonic nozzle arranged above this stable location is intermittently activated to generate a spray dust of coating liquid that falls down onto the sphere and forms a coating thereon. This type of nozzle generates a spray of droplets, the velocity of which is adjusted by means of a separate air flow through the nozzle. The apparatus is used for investigating the influence of different parameters, such as droplet velocity, temperature of fluidizing air, drying time, and type of coating liquid, on the thickness and morphology of the resulting coating. A rough measurement value of the overall thickness of the coating is obtained by weighing the sphere before and after the actual coating process and determining the difference in weight. The morphology of the coating is qualitatively examined by arranging the sphere, once coated, in a scanning-electron-microscope (SEM). For both of these measurements, the sphere must be removed from the apparatus for analysis. The apparatus also includes a lamp for illumination of the sphere and a video camera for continuous and qualitative observation of the continuous of the sphere during the coating process.

One drawback of this prior-art apparatus resides in the difficulty to make quantitative, time-resolved measurements of coating properties. After a specific time period, the coating process must be interrupted for analysis of the coating on tile sphere, whereupon a new and non-coated sphere must be subjected to a new coating process for a longer time period, and so on. In this approach, the formation of a coherent time series of measurement data requires that identical conditions are maintained in the environment of each sphere. Thus, the coating process must be repeated in exactly the same manner for each sphere. This is difficult. For example, any small variations in the masses of the aluminum spheres will necessitate an adjustment in the flow rate of the fluidizing air, to maintain each sphere at the same location in the vessel. Such a change in now rate will also change the environment of the sphere during the coating process, thereby making it difficult to compile the measurement data from several consecutive measurements into a coherent time series.

A further drawback of this known apparatus is that only a few properties of the coating, i.e. average thickness and surface morphology, can be measured.

Another drawback is that the course of a coating process can only be studied on standardized spheres, so that the coating process can be repeated in exactly the same manner for each sphere. However, the coating process is believed to be highly dependent on the properties of the particle itself, such as the size, density, porosity and shape of the particle. Thus, it may be difficult, or even impossible, to draw any conclusions lot a realistic particle from experiments made in the known apparatus.

SUMMARY OF THE INVENTION

The object of the invention is to solve or alleviate some or all of the problems described above. More specifically, the method and apparatus according to the invention should allow for time-resolved measurements of coating properties on any type of particle.

This object is achieved by the method and apparatus set forth in the appended claims.

The inventive method and apparatus will allow for continuous and non-invasive monitoring of one or more principal parameters related to the coating, such as thickness, thickness growth rate and physical and/or chemical properties related to the quality of the coating, as well as heat, mass and momentum transfer, during the coating process on a single particle. The results of the measurements made possible by the inventive apparatus and method can be used to develop a fundamental model of the coating process on a single particle as a function of one or more control parameters, which can be related to properties of the environment of the particle and to properties of the particle itself. Ultimately, such a fundamental model can be converted to an aggregate model for prediction of the influence of global process parameters on the monitored principal parameter or parameters for a large number of particles, for example in a full-scale coating process in an industrial plant. Such an aggregate method is a valuable tool that can be used to scale up processes and plants, improve existing ,manufacturing processes and plants, and develop new products.

It should also be noted that the invention allows for monitoring of the coating process on any type of single solid sample. Thus, in contrast to prior art technique, it is conceivable to use a realistic nucleus, such as a pellet, a tablet, or a capsule.

The inventive method and apparatus have the additional advantage of providing information that can be directly used in the control of a full-scale process. More specifically, by effecting a coating process on a single particle at well-controlled conditions, so that desired properties of the coating on the particle is obtained, and by continuously performing the spectrometric measurement, a desired sequence of measurement values can be obtained. By effecting the same spectrometric measurement in a full-scale process, the global process parameters of this process can be controlled to yield the desired sequence of measurement values. Thereby, the full-scale process will be controlled to yield the desired properties of the coating on the particles. In practice, the sequence of measurement values could form a desired trajectory in a space that is defined by one or more principal components. These principal components can be derived by applying chemometric methods to measurement data obtained from a time-series of spectrometric measurements. Evidently, the desired sequence of measurement values could also be established by effecting a spectrometric measurement on a batch of particles in the full-scale process itself. However, by means of the invention, the desired sequence of measurement values is established much faster, since the coating process of a single particle is considerably shorter in time than the coating process of a batch of particles in a full-scale process.

In an alternative approach for direct control of a full-scale process, the inventive method and apparatus are used to identify the interrelationship between control parameters, given by conventional sensors, and principal parameters, given by spectrometric methods. This is typically done by effecting a coating process on a single particle at well-controlled conditions, and by continuously performing a spectrometric measurement and simultaneously performing a measurement of one or more control parameters, such as a fluidizing gas flow rate or a temperature. By identifying relevant control parameters in this way, the inventive method and apparatus could be used to establish a desired sequence of control parameter values. This sequence could then be directly transferred to a full-scale process, wherein the global process parameters of this process are controlled to form a corresponding desired sequence of global process parameter values. Thereby, the full-scale process will be controlled to yield the desired properties of the coating on the particles.

Preferably, the step of forming the coating on the particle includes generating a single droplet of a coating fluid and making the droplet impinge on the particle. The use of a single droplet, or a sequence of such single droplets, instead of a spray dust, provides for a controlled deposition of coating fluid on the particle surface. Thus, the droplet size or the droplet generating rate can be controlled during a wetting period and be used as well-defined control parameters. The ten "coating fluid" is used as a comprehensive expression encompassing everything from a pure coating liquid to a slurry or suspension of coating liquid and coating solids. Alternatively, the coating fluid could be a mixture of coating solids and a carrier gas. In this case, the term "coating droplet" would refer to a coating solid.

Preferably, (he particle is fluidized on an upwardly directed gas flow, so that the particle is held at a given spatial location, while being freely rotatably at this location. Thus, the particle can be fixed so that a precise measurement can be effected, and rotating so that a uniform coating can be formed. The fluidizing gas flow has the additional function of drying the particle.

It is preferred that each droplet upon generation is moved into and allowed to follow the fluidizing gas flow to the particle. Thereby it is assured that each droplet impinges on the fluidized particle.

In another preferred embodiment, the control parameter is changed based, at least partly, on the measurement value. This type of feed-back control provides for in-line adjustments of the coating process on the single particle. Thereby it is possible to monitor the effects of a change in any control parameter during the coating process.

The control parameter could include a property of said gas flow, such as a flow rate, a temperature or a content of a solvent, for example water; a property on the particle, such as a size, a shape, a density or a porosity; a property of the droplets, such as a droplet size, a droplet generation rate or a concentration of a droplet constituent; a duration of a wetting period during the coating process; and a duration of a drying period during the coating process. In addition to the control parameters listed above, there arc also other parameters not listed here.

Preferably, the spectrometric measurement is performed by means of near infrared spectrometry and or a spectrometric method based on Raman scattering and/or a spectrometric method based on absorption in the UV, visible, or infra-red (IR) wavelength region, or luminescence, Such as fluorescence emission, and/or imaging spectrometry.

BRIEF DESCRIPTION OF THE DRAWINGS

In the following, a presently preferred embodiment of the invention, will be described in more detail, reference being made to the accompanying drawing which schematically shows a layout of a monitoring apparatus.

DESCRIPTION OF THE PREFERRED EMBODIMENT

The monitoring apparatus disclosed on the drawing comprises a coating chamber 1, a gas supply unit 2, a coating liquid dispenser 3, a spectrometric measurement unit 4, and a main control unit 5. In the coating chamber 1, the coating process of a single particle P can be continuously and non-invasively monitored under well-controlled conditions.

A vertical tube 6 extends from a bottom portion 7 of the chamber 1 along a vertical center line of the chamber 1. The gas supply unit 2 is adapted to feed a gas in controlled amounts to the chamber 1. The unit 2 communicates with the tube 6 and a periphery portion 8 of the chamber 1. The flow of gas through the tube 6 is used to levitate or fluidize the particle at a given position in the chamber 1. The flow of shielding gas to the periphery portion 8 is used to minimize any gradients between the measurement unit 4 and the particle P, since such gradients might introduce errors in the spectrometric measurements. Although not shown on the drawing, it is realized that such shielding gas could be supplied to the periphery portion 8 at several locations around the perimeter of the chamber 1. Alternatively, or additionally, shielding gas could be fed through the bottom portion 7.

A control system is provided to accurately position the particle P. The control system includes a position sensor 9, for example an array detector, which is arranged at the periphery of the chamber 1 and is adapted to output a position signal indicating to the position of the particle P. The position signal is fed to the main control unit 5, which adjusts the gas flow rate accordingly by feeding a control signal to the gas supply unit 2. The control system is capable of maintaining the particle P at a given position in the chamber 1. This position might be changed over time in a controlled manner, or be spatially fixed in the chamber 1.

The gas supply unit 2 is also adapted to condition the gas, for example lay changing the gas temperature or the gas content of a solvent, such as water, based on corresponding control signals received from the main control unit 5. To this end, the gas supply unit 2 could include a conventional bubbler system (not shown), in which the gas is bubbled through a liquid source to add a small concentration of liquid vapor to tile gas. Such, and other, high-precision systems for fixing gas and liquid vapor are available on the market.

One or more coating liquid dispensers 3 (only one shown on the drawing) is connected to the tube 6 and is adapted to sequentially generate droplets D of a coating liquid. The generated droplets D are injected into the gas flow in the tube 6 and will, by following the gas flow to the particle P, impinge on the particle P and form coating thereon. The coating liquid dispenser 3 receives control signals, indicating for example the desired droplet generation rate and droplet size, from the main control unit 5.

In the illustrated example, the coating liquid dispenser 3 is a flow-through microdispenser of the type disclosed in the article "Design and development on a silicon microfabricated flow-through dispenser for on-line picolitre sample handling", Journal of Micromechanical Microengineering No. 9, pp 369–376, 1999, by T. Laurell, L. Wallman and J. Nilsson. This microdispenser, of which no details are given in the drawing, comprises two joined silicon structures forming a flow-through channel. A piezoceramic element is connected to one of the silicon structures. By activating the piezoceramic element, a pressure pulse is generated in the channel, thereby ejecting a droplet from an orifice in the opposite silicon structure. This microdispenser allows for sequential generation of droplets with a well-defined size and frequency.

The spectrometric measurement unit 4 is arranged at the periphery of the chamber 1 and is adapted to performing a spectrometric measurement, preferably by NIRS (Near Infrared Spectrometry), on the coating during the coating process. The resulting measurement data are represented in a sample vector. The spectrometric measurement unit 4 is also adapted to evaluate the measurement data in the sample vector and derive a measurement value related to the coating. This measurement value is fed to the main control unit 5 for storage.

NIRS provides both physical and chemical properties of the coating. This spectrometric method, like several other commonly used spectrometric methods, is non-invasive as well as non-destructive. A NIRS measurement is fast and therefore, it is employable for continuously measuring samples of all kinds. The possibilities obtained by NIRS measurements will be further discussed below.

Further, with a spectrometric measurement according to the invention, it is possible to extract information from several different depths of the coating, i.e. from the surface as well from deeper levels thereof. Additionally, it is possible to directly measure the thickness of the coating. The spectrometric measurement can be carried out in such a manner that the particle l, the coating thickness of which is to be measured, is positioned at a desired level with respect to the measurement unit 4. Thus, the mean coating thickness or a variation of the coating thickness can be measured. By employing imaging spectrometry, local inhomogeneities in the coating can be measured. Imaging spectometry also allows for variations in the position of the particle P during the spectrometric measurement.

In the spectrometric measurement unit 4, the sample vector is evaluated in order to extract information directly related to the quality of the coating. in one embodiment, the evaluation is performed by subjecting the sample vector to a mathematical analysis, weighting the data, in conjunction to previous data, and condensing them to at least one measurement value. In the present embodiment chemometric methods are used. More particularly and at least in the case of continuous measurements during the coating process, a multivariate analysis, such as PCA (Principal Component Analysis), or PLS (Partial Least Squares) is performed on the sample vector.

In this way, it is possible to directly measure the quality of the coating, in terms of relevant physical and/or chemical properties. As a further example, the heat transfer to the coating can be monitored by way of extracting a measurement value related to the surface temperature of the coating. Further, the mass transfer to the coating can be monitored by way of extracting a measurement value related to the moisture content of the coating.

The main control unit 5, for example a personal computer, is adapted to continuously store control parameters potentially affecting the coating process on the particle P in the chamber 1. Some control parameters are mentioned above, for example the gas temperature, the gas humidity, the droplet generation rate, and the droplet size. The main control unit receives additional control parameter information from a temperature sensor 10a, a mass flow meter 11 and a gas analyzer 12 arranged to measure the temperature, the flow rate and the solvent concentration, respectively, of the gas entering chamber 1 through tube 6, as well as a temperature sensor 13 and a gas analyze 14 arranged to measure the temperature and the solvent concentration, respectively, of the gas leaving chamber 1. Additionally, a temperature sensor 10b is arranged to measure the temperature of the shielding gas entering the chamber 1. Other such conventional sensors could be provided. Further control parameters could include tile duty cycle of the coating liquid dispenser 3, i.e. the time period with wetting and drying, respectively, of the particle P. Further control parameters could be related to the particle P itself, or the concentration of a constituent of the coating liquid.

It is appreciated that one or more control parameters could be changed during the coating process, for monitoring its influence on the properties of the coating, as measured by the unit 4.

Examples of possible modifications comprise for example the use of the spectrometric methods, such as those based on Raman scattering, or absorption in the UV and visible or infrared (IR) wavelength regions or luminescence such as fluorescence emission.

Another example of a modification substitutes a more simple analysis to the chemometric methods as follows. Generally, when using spectrometric methods, broad response spectra are obtained. However, instead of analysing all of the measurement values obtained over such a broad response spectrum by applying chemometric methods, merely one or a few values of the measurement values arc analysed. For example, the measurement values at a few individual frequencies could be analysed. Also, when employing Raman spectrometry, which often results in values well separated by wavelength, this simplified analysis can be useful.

What is claimed is:

1. A method for monitoring the formation of a coating on a single particle, comprising the steps of:
    (a) arranging the particle at a given spatial location, wherein the step of arranging the particle comprises fluidizing the particle on an upwardly directed gas flow;
    (b) forming the coating on the particle at the given spatial location; and
    (c) performing a spectroscopic measurement on the coating while the coating is being formed on the particle to obtain a measurement value of at least one principal parameter related to the coating.

2. The method as set forth in claim 1, wherein the spectrometric measurement is preformed continuously during at least pert of the coating formation step to generate a sequence of measurement values of the principal parameter.

3. The method as set forth in claim 1, wherein the coating formation comprises generating a single droplet eta coating fluid, and bringing the droplet to impinge upon the particle.

4. The method as set forth in claim 3, wherein the droplet upon generation is moved into and allowed to follow the upwardly directed gas flow to the particle.

5. The method as set forth in claim 3, wherein the step of generating a single droplet is repeated, thereby forming at least one stream of droplets which sequentially impinge upon the particle.

6. The method as set forth in claim 1, further comprising the steps of:
    monitoring at least one control parameter related to the particle or its environment; and
    identifying a functional relationship between the control parameter and the principal parameter.

7. The method as set forth in claim 6, further comprising the step of generating an aggregate model for prediction of the influence of the control parameter on the principal parameter for a large number of particles based on the functional relationship for the single particle.

8. The method as set forth in claim 6, further comprising the step of adjusting the control parameter at least partly on the basis of the measurement value.

9. The method as set forth in claim 1, further comprising the steps of:
    a) monitoring at least one control parameter related to the particle or its environment; and
    b) identifying a functional relationship between the control parameter and the principal parameter,
wherein the control parameter comprises a property of the gas flow.

10. The method as set forth in claim 6, wherein the control parameter comprises a property of the particle.

11. The method as set forth in claim 3, further comprising the steps of:
    monitoring at least one control parameter related to the particle or its environment; and
    identifying a functional relationship between the control parameter and the principal parameter,
wherein the control parameter comprises a property of the droplet.

12. The method as set forth in claim 3, further comprising the steps of:
    monitoring at least one control parameter related to the particle or its environment; and
    identifying a functional relationship between the control parameter and the principal parameter,
wherein the control parameter comprises the duration of a wetting period during the coating formation step.

13. The method as set forth in claim 3, further comprising the steps of:
    monitoring at least one control parameter related to the particle or its environment; and
    identifying a functional relationship between the control parameter and the principal parameter,
wherein the control parameter comprises the duration of a drying period during the coating formation step.

14. The method as set forth in claim 1, wherein the step of obtaining the measurement value comprises:

c1) generating a sample vector of measurement data from the spectrometric measurement; and e2) condensing the measurement data into the measurement value of the principal parameter.

15. The method as set forth in any one of claims 1, 2 and 3-14, wherein the spectrometric measurement is performed by means of near-infrared spectrometry.

16. The method as set forth in any one of claims 1, 2 and 3-14, wherein the spectrometric measurement is performed by means of a spectrometric method based on Raman scattering.

17. The method as set forth in any one of claims 1, 2 and 3-14, wherein the spectrometric measurement is performed by means of a spectrometric method based on absorption in the UV, visible, or infrared (IR) wavelength region, or luminescence or fluorescence emission.

18. The method as set forth in any one of claims 1, 2 and 3-14, wherein the spectrometric measurement is performed by means of imaging spectrometry.

19. The method as set forth in any one of claims 1, 2 and 3-14, wherein the particle is a pharmaceutical product.

20. A method for controlling the coating process of a batch of particles, comprising the steps of:

a) monitoring the coating formation according to claim 2;

b) using the sequence of measurement values of the principal parameter as a sequence of reference values in the control; and c) obtaining a corresponding spectroscopic measurement on the batch of particles to provide a sequence of actual values for the control.

21. A method for controlling the coating process of a batch of particles, comprising the steps of:

a) monitoring the coating formation according any one of claims 1, 2 and 3-14;

b) identifying a functional relationship between at least one principal parameter and at least one simultaneously-monitored control parameter, wherein the control parameter is related to an environment of a single particle of the batch;

c) selecting one or more control parameters, based on the functional relationship, to represent one or more of the principal parameters;

d) determining a desired sequence of values of the selected control parameter(s) for the single particle; and e) controlling the coating process of the batch of particles based on the desired sequence of selected control parameter values.

22. An apparatus for monitoring the formation of a coating of a single particle comprising:

means for winging the particle at a given spatial location, wherein the means comprises a flow unit which generates a fluidized gas flow upon which the particle is fluidized;

a fluid supply unit for applying a coating fluid to the particle to form a coating at the given spatial location; and a measurement unit which performs a spectrometric measurement on the coating while the coating is being formed on the particle and derives a measurement value of at least one principal parameter related to the coating.

23. The apparatus as set forth in claim 22, wherein the measurements unit continuously performs the spectrometric measurement and thereby generates a sequence of measurement values of the principal parameter.

24. The apparatus as set forth in claim 22, further comprising a chamber in which the coating is formed on the particle, wherein the flow unit provides a shielding gas inside the chamber intermediate the measurement unit and the location of the particle, and wherein the shielding gas is substantially identical to the gas used for fluidizing the particle.

25. The apparatus as set forth in claim 22, wherein the fluid supply unit generates a single droplet of the coating fluid which is brought to impinge upon the particle.

26. The apparatus as set forth in claim 25, wherein the fluid supply unit injects each droplet of the coating fluid into the fluidizing gas flow.

27. The apparatus as set forth in claim 25, wherein the fluid supply unit repeatedly generates single droplets of the coating fluid and thereby forms a stream of such droplets which sequentially impinge upon the particle.

28. The apparatus as set forth in claim 22, further comprising a control unit which monitors at least one control parameter related to the particle or its environment.

29. The apparatus as set forth in claim 28, wherein the control unit receives the measurement value from measurement unit and adjusts the control parameter at least partly on the basis of the measurement value.

30. The apparatus as set forth in claim 28, wherein the control unit receives the measurement value from the measurement unit and adjusts the control parameter at least partly on the basis of the measurement value; and wherein the control parameter comprises a property of the fluidizing gas flow, and the control unit adjusts the control parameter by controlling the flow unit.

31. The apparatus as set forth in claim 28, wherein the control unit receives the measurement value from the measurement unit and adjusts the control parameter at least partly on the basis of the measurement value; and wherein the control parameter comprises a property of the droplet, and the control unit adjusts the control parameter by controlling the fluid supply unit.

32. The apparatus as set forth in claim 28, wherein the control unit receives the measurement value from the measurement unit and adjusts the control parameter at least partly on the basis of the measurement value; and wherein the control parameter comprises the duration of droplet generation period; and the control unit adjusts the control parameter by controlling the fluid supply unit.

33. The apparatus as set forth in claim 28, wherein the control unit receives the measurement value from the measurement unit and adjusts the control parameter at least partly on the basis of the measurement value; and wherein the control parameter comprises the duration of a drying period, and the control unit adjusts the control parameter by controlling the fluid supply unit.

34. The apparatus as set forth in any one of claims 22, 23 and 24-33, wherein the measurement unit performs the spectrometric measurement by means of near-infrared spectrometry.

35. The apparatus as set forth in any one of claims 22, 23 and 24-33, wherein the measurement unit performs the spectrometric measurement by means of a spectrometric method based on Raman scattering.

36. The apparatus as set forth in any one of claims 22, 23 and 24-33, wherein the measurement unit performs the spectrometric measurement by means of a spectrometric method based on absorption in the UV, visible, or infrared (IR) wavelength region, or luminescence or fluorescence emission.

37. The apparatus as set forth in any one of claims 22, 23 and 24-33, wherein the measurement unit performs the spectrometric measurement by means of imaging spectrometry.

38. The method as set forth in any one of claims 22, 23 and 24-33, wherein the particle is a pharmaceutical product.

39. The method as set forth in claim 4, further comprising the steps of:
   a) monitoring at least one control parameter related to the particle or its environment; and
   b) identifying a functional relationship between the control parameter and the principal parameter;
wherein the control parameter comprises a property of the flow.

40. The method as set forth in claim 9, wherein the property of the gas flow is flow rate, temperature, or solvent content.

41. The method as set forth in claim 39, wherein the property of the gas flow is flow rate, temperature, or solvent content.

42. The method as set forth in claim 10, wherein the property of the particle is size, shape, density, or porosity.

43. The method as set forth in claim 11, wherein the property of the droplet is size, generation rate, or concentration of a constituent.

44. The method as set forth in claim 12, wherein the wetting period is effected by controlling the droplet generation.

45. The method as set forth in claim 19, wherein the pharmaceutical product is a pellet, a tablet, a capsule.

46. The apparatus as set forth in claim 28, wherein the control unit receives the measurement value from the measurement unit and adjusts the control parameter at least partly on the basis of the measurement value; and wherein the control parameter comprises a property of the fluidizing gas flow, and the control unit adjusts the control parameter by controlling the flow unit.

47. The apparatus as set forth in claim 30, wherein the property of the fluidizing gas flow is flow rate, moisture content, or temperature.

48. The apparatus as set forth in claim 46, wherein the property of the fluidizing gas flow is flow rate, moisture content, or temperature.

49. The apparatus as set forth in claim 31, wherein the property of the droplet is size, generation rate, or concentration of a constituent.

50. The apparatus as set forth in claim 38, wherein the pharmaceutical product is a pellet, tablet, or capsule.

* * * * *

UNITED STATES PATENT AND TRADEMARK OFFICE
CERTIFICATE OF CORRECTION

PATENT NO. : 6,946,157 B2
DATED : September 20, 2005
INVENTOR(S) : Folestad et al.

It is certified that error appears in the above-identified patent and that said Letters Patent is hereby corrected as shown below:

Column 8,
Line 6, "preformed" should read -- performed --.
Line 7, "pert" should read -- part --.
Line 10, "eta" should read -- of a --.

Column 9,
Line 54, "winging" should read -- arranging --.
Line 63, insert -- , -- after "particle".
Line 67, "measurements" should read -- measurement --.

Column 10,
Line 23, "from" should read -- from the --.
Line 44, "of" should read -- of a --.

Column 11,
Line 15, "flow" should read -- gas flow --.

Column 12,
Line 5, "a capsule" should read -- or a capsule --.

Signed and Sealed this

Twenty-seventh Day of December, 2005

JON W. DUDAS
*Director of the United States Patent and Trademark Office*